United States Patent
Boyd

(10) Patent No.: US 10,123,764 B2
(45) Date of Patent: Nov. 13, 2018

(54) VIBRO-ACOUSTIC TRANSDUCER

(71) Applicant: Coleridge Design Associates LLC, San Jose, CA (US)

(72) Inventor: Geoffrey A. Boyd, San Jose, CA (US)

(73) Assignee: COLERIDGE DESIGN ASSOCIATES LLC, San Jose, CA (US)

( * ) Notice: Subject to any disclaimer, the term of this patent is extended or adjusted under 35 U.S.C. 154(b) by 0 days.

(21) Appl. No.: 15/471,812

(22) Filed: Mar. 28, 2017

(65) Prior Publication Data
US 2018/0279987 A1    Oct. 4, 2018

(51) Int. Cl.
| A61B 7/04 | (2006.01) |
| H04R 7/18 | (2006.01) |
| H04R 9/08 | (2006.01) |
| H04R 1/46 | (2006.01) |

(52) U.S. Cl.
CPC .............. *A61B 7/04* (2013.01); *H04R 1/46* (2013.01); *H04R 7/18* (2013.01); *H04R 9/08* (2013.01)

(58) Field of Classification Search
CPC ..... A61B 7/04; A61B 7/02; A61B 2562/0204; H04R 1/46; H04R 7/18; H04R 9/08
See application file for complete search history.

(56) References Cited

U.S. PATENT DOCUMENTS

| 3,160,708 | A | * | 12/1964 | Andries | A61B 7/04 181/131 |
| 4,258,229 | A | * | 3/1981 | Eggert | H04R 17/02 381/67 |
| 4,903,794 | A | * | 2/1990 | Klippert | A61B 7/02 181/131 |
| 5,913,829 | A | * | 6/1999 | Reeves | A61B 7/003 600/528 |
| 6,726,635 | B1 | * | 4/2004 | LaSala | A61B 7/04 181/131 |
| 2009/0211838 | A1 | * | 8/2009 | Bilan | A61B 7/04 181/131 |
| 2010/0290660 | A1 | * | 11/2010 | Fukuda | H04R 7/122 381/355 |

* cited by examiner

*Primary Examiner* — Andrew L Sniezek
(74) *Attorney, Agent, or Firm* — Morgan, Lewis & Bockius LLP

(57) ABSTRACT

In various embodiments, vibro-acoustic transducer arrangements in accordance herewith are optimized for sensing and transducing acoustic phenomena occurring within a patient's body, and manifesting themselves at the skin surface with frequencies ranging from 0.001 Hz to 10 kHz. Strategies for effectively coupling to the skin include judicious mismatching of mechanical impedance, the use of impedance-matching gels or liquids, a shaped (e.g., domed) pickup, material selection, and/or a peripheral leaf-spring arrangement permitting relative movement between inner and peripheral diaphragm portions. The spring stiffness or spring compliance of the leaf springs may be selectively chosen to optimize the frequency response of the sensor.

22 Claims, 15 Drawing Sheets

VIBRO-ACOUSTIC TRANSDUCER

FIELD OF THE INVENTION

The present invention relates to electromechanical vibro-acoustic devices generally and in particular to systems that utilize electrodynamic transducers coupled to the external surfaces of biological tissue for, e.g., the non-invasive recording, storage, analysis and playback of internal body sounds produced by living creatures.

BACKGROUND

The stethoscope was invented in France in 1816 by René Laennec for the purpose of auscultation, i.e., listening for sounds produced within the body mainly to assess the condition of organs and vessels including the heart, lungs, aorta, and intestines. Fetal heart tones can also be monitored during pregnancy by auscultation with specialized stethoscopes. Blood flow in blood vessels can also be auscultated. Auscultation performed with the unaided ear is called immediate or direct auscultation, and when a stethoscope is used it is called mediate auscultation.

The electronic stethoscope is the updated version Laennec's concept where a skin-contact diaphragm creates an acoustic chamber in which airborne sounds are converted to electrical signals. These signals are amplified, filtered or otherwise processed, and played through, e.g., a loudspeaker or earpiece. A significant amount of bodily sound information is in the frequency band 0.001 Hz to 100 Hz, and because the threshold of audibility rises sharply below 100 Hz, the amplification of the electrical signals to make them audible becomes difficult if not futile. Few current systems, even electronic stethoscope systems, have been designed for accurate and effective amplification within this range.

SUMMARY

In various embodiments, vibro-acoustic transducer arrangements in accordance herewith are optimized for sensing and transducing acoustic phenomena occurring within a patient's body, and manifesting themselves at the skin surface with frequencies ranging from 0.001 Hz to 10 kHz. Strategies for effectively coupling to the skin include judicious mismatching of mechanical impedance, the use of impedance-matching gels or liquids, a shaped (e.g., domed) pickup, material selection, and/or a peripheral leaf-spring arrangement permitting relative movement between inner and peripheral diaphragm portions. The spring stiffness or spring compliance of the leaf springs may be selectively chosen to optimize the frequency response of the sensor.

Accordingly, in a first aspect, the invention pertains to a sensor device. In various embodiments, the sensor device comprises a diaphragm having an outer peripheral portion and an inner portion, the inner movable portion being attached to the outer portion by a plurality of leaf springs constraining relative movement between the inner portion and the peripheral portion; a coil disposed over at least one side of the diaphragm; and at least one magnet operatively disposed with respect to the coil to cause current to flow through the coil upon relative movement between the movable portion and the peripheral portion.

In some embodiments, the inner portion is fixed and the outer peripheral portion is movable with respect thereto; in other embodiments, the outer portion is fixed and the inner peripheral portion is movable with respect thereto. For example, in a particular embodiment, the outer fixed portion of the diaphragm has a shape and the inner movable portion is defined within a plurality of slots through the diaphragm and arranged in a series. The series defines a closed sequence concentric with and having the shape of the outer fixed portion, and each pair of slots is parallel and has an overlap portion and a non-overlap portion, the overlap portion defining an intervening strip corresponding to one of the leaf springs. In some cases, the slots are filled with a thixotropic material. In some embodiments, the coil and the at least one magnet are circular, while in other embodiments, one or both have a different shape.

In some embodiments, the magnets are a pair of magnet assemblies disposed on opposite sides of the diaphragm, each of the assemblies including at least two concentric magnets. Each of the magnets may have an isosceles trapezoid cross-section with an angle of 45°±5°. In various embodiments, the coil occupies 50% to 75% of the diaphragm area.

The sensor device may include a pickup structure extending from the diaphragm for contact with a biological tissue surface. The diaphragm may have modal contributions with zero mean volume velocity to isolate a pistonic response of the diaphragm for voltage generated in a direction perpendicular to the diaphragm. In some embodiments, the diaphragm is a composite sandwich panel including a core and a monolithic panel on each side of the core. For example, the panels may be copper foil-clad flexible printed circuit polymer film. The copper may be etched to ensure isotropic mechanical impedance of 10% or less of a shortest planar dimension of the diaphragm. In some embodiments, the panels are fabricated from a graphene composite structure, and the graphene may be etched to ensure isotropic mechanical impedance of 10% or less of a shortest planar dimension of the diaphragm.

In some embodiments, the diaphragm is asymmetrically biased in an unenergized state. The bias may, for example, be in the range of 0.1 mm to 3 mm. The pickup structure may be dome-shaped, and may or may not have surface features. If so, the surface may pimpled, dimpled and/or corrugated. The pickup structure may have a mechanical impedance mismatched with respect to a target surface.

In another aspect, the invention relates to a sound transducer. In various embodiments, the sound transducer comprises a diaphragm comprising a peripheral portion and a central domed pickup portion; a retention member surrounding the diaphragm and configured to retain the diaphragm while permitting movement of at least a portion thereof when acoustic energy is imparted to the domed pickup portion; and a transducer for converting movement of at least a portion thereof into an electrical signal.

The peripheral portion may be flat or, in some embodiments, an extension or peripheral edge of the dome. In various embodiments, the transducer comprises at least one coil attached to the diaphragm and at least one magnet separate from the diaphragm but magnetically coupled to the coil. In other embodiments, the diaphragm is capacitive. The pickup portion may have a mechanical impedance mismatched with respect to a target surface.

In some embodiments, the sensor is coupled to a Pinard horn—a cone-shaped fetoscope that amplifies the sound of fetal heartbeats or newborn heartbeats and has been described as a type of "ear trumpet" (whereby the longer cones (as long as 30") lose clarity in the signal but are better at picking up faint heart sounds). An embodiment with binaural fetoscopes allows users to hear the heartbeat through both ears or can be recorded for reproduction in stereo. In one embodiment, the transducer is connected to a cone-shaped device with the larger-diameter end of the cone configured for placement on the chest wall.

As used herein, the terms "approximately" and "substantially" mean±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description of the invention in conjunction with the drawings, wherein.

DETAILED DESCRIPTION

Figure 1A:
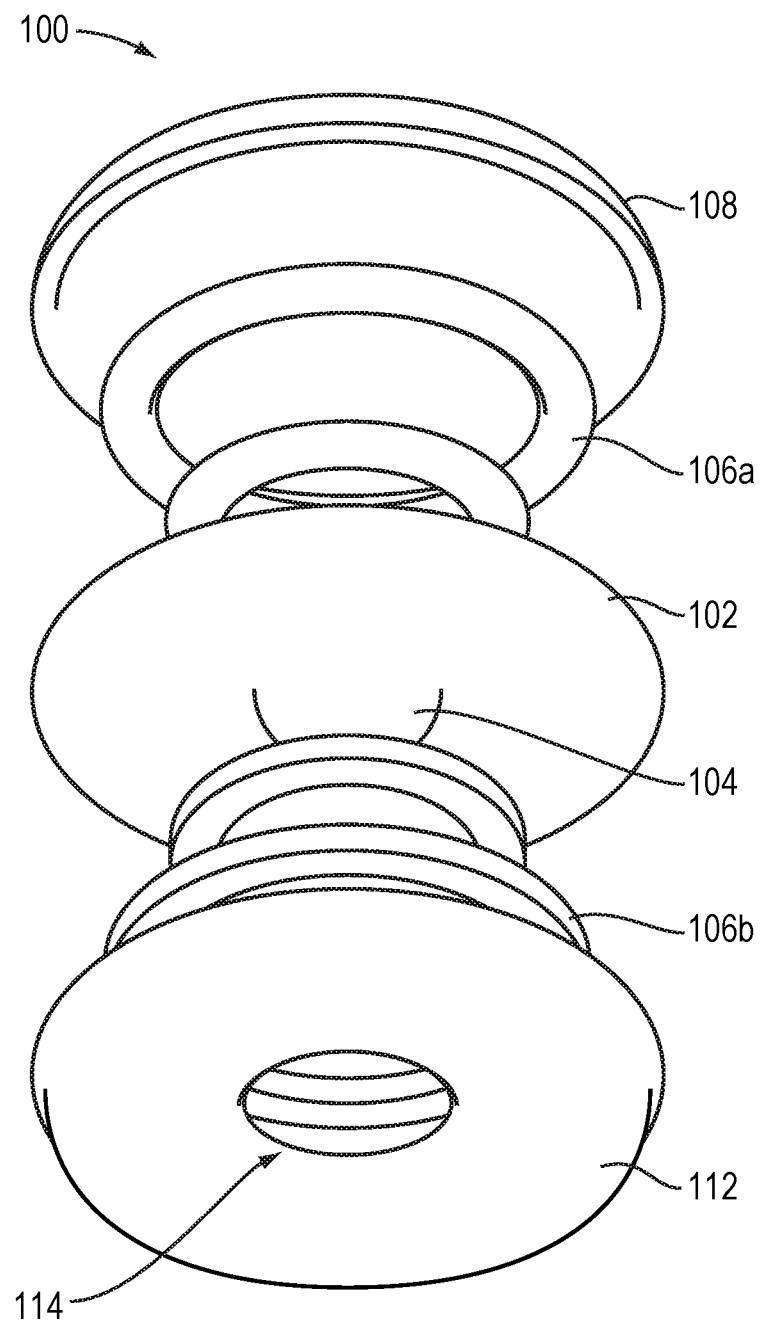
FIG. 1A shows an exploded view of a vibro-acoustic sensor in accordance with an embodiment of the invention.
Figure 1B:
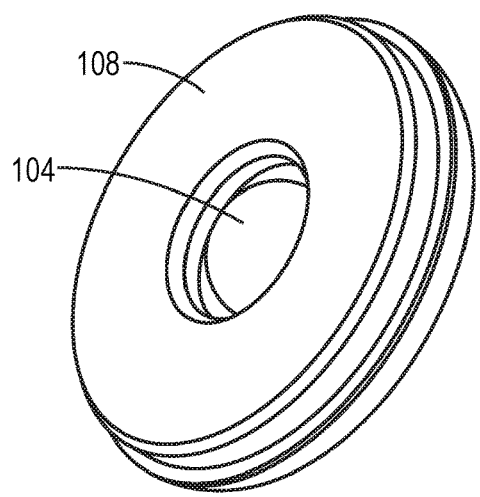
FIGS. 1B and 1C are perspective and sectional elevational views, respectively, of the sensor shown in FIG. 1A.

A vibro-acoustic sensor in accordance herewith is shown in FIG. 1A at 100. The sensor 100 includes a diaphragm 102 with an integrated pickup 104 (e.g., a dome), a top magnet assembly 106a and a bottom magnet assembly 106b operatively disposed relative to the diaphragm 102. A top housing portion 108 is disposed over the top magnet assembly 106a, and a bottom housing portion 112 is disposed below the bottom magnet assembly 106b and includes a central opening 114. As illustrated in FIG. 1B, when the sensor 100 is assembled, the central portion of the pickup 104 protrudes through the central opening 114 of the bottom housing portion 112.

With reference to FIGS. 2A-2D, in one embodiment, the diaphragm 102 is a planar substrate with a dome. Although the diaphragm 102 is a single mechanical fixture, functionally it has a fixed peripheral (here, annular) portion 202 with peripheral mounting holes and a central portion 204 movable with respect to the fixed peripheral portion. In some embodiments, the peripheral portion 202 is movable relative to the central portion 204. In the illustrated embodiment, movability between the fixed portion 202 and the movable portion 204 is conferred by a closed-shape (here circular) sequence of circumferentially overlapping slots representatively indicated at 206. These may be formed, for example, by laser cutting. By "overlap" is meant that each parallel pair of slots has corresponding portions that are directly opposed to each other and remaining portions that extend lengthwise beyond the other slot of the pair. A coil 208 is disposed over the movable portion 204 of the diaphragm 102. Relative movement between the coil 208 and the magnet(s) induces a current through the coil that is related, typically linearly, to the degree of displacement of the diaphragm. Alternative embodiments include a diaphragm 102 with various non-planar curvatures and or corrugations. Moreover, if the diaphragm 102 has a non-circular shape as discussed below, the sequence of slots 206 will conform to that shape.

The intervening strip of material 218 defined by the overlap between each pair of slots 206 functions as a leaf spring during operation. This leaf spring provides mechanical compliance with respect to vibratory movement of the movable portion 204 (into and out of the page). The degree of compliance is determined by the width of the slots 206, their number, their length and the length and width of the overlap portion 218. The spring stiffness or spring compliance may be selectively chosen to optimize the frequency response of the sensor, within a certain range of frequencies. A typical working range of slot width is 0.1 mm to 1 mm for a one-inch (25 mm) diaphragm 102, with approximately linear scaling for larger- or smaller-diameter diaphragms.

The slots are additionally advantageous in reducing the total material content of the diaphragm 102, thereby increasing its responsiveness to vibrations transferred from the pickup 104. There is no need for the diaphragm to propagate sound waves through air or other medium, and therefore it is unnecessary to minimize the surface area of the slots on the diaphragm 102 or to create a discrete separation between the anterior and posterior portion of the diaphragm. In some embodiments, the slots are filled with a thixotropic material, such as high-vacuum silicone grease, that softens with increasing vibration frequency. The objective is to allow for sufficient diaphragm displacement together with viscoelastic damping at the diaphragm edge.

Figure 2A:
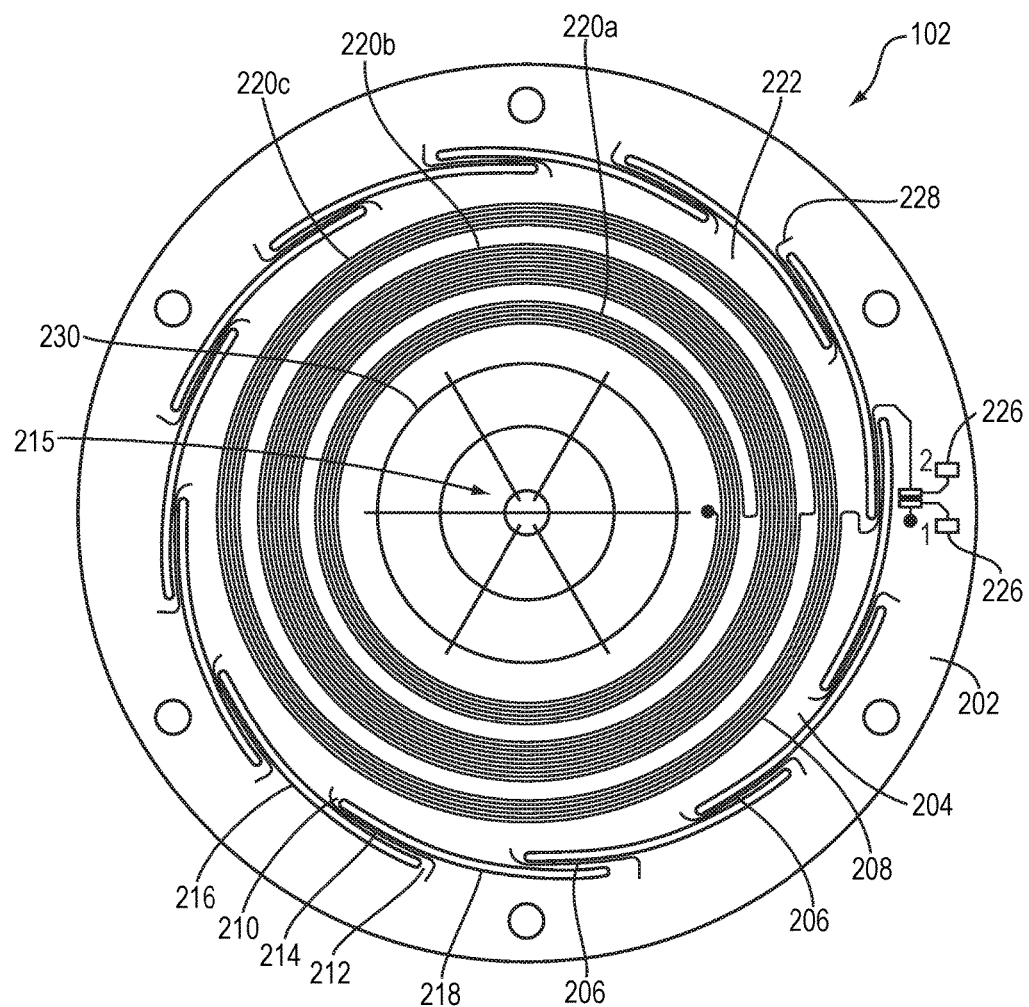
FIG. 2A is a top plan view of the interior of the diaphragm illustrated in FIGS. 1A-1C.
Figure 2B:
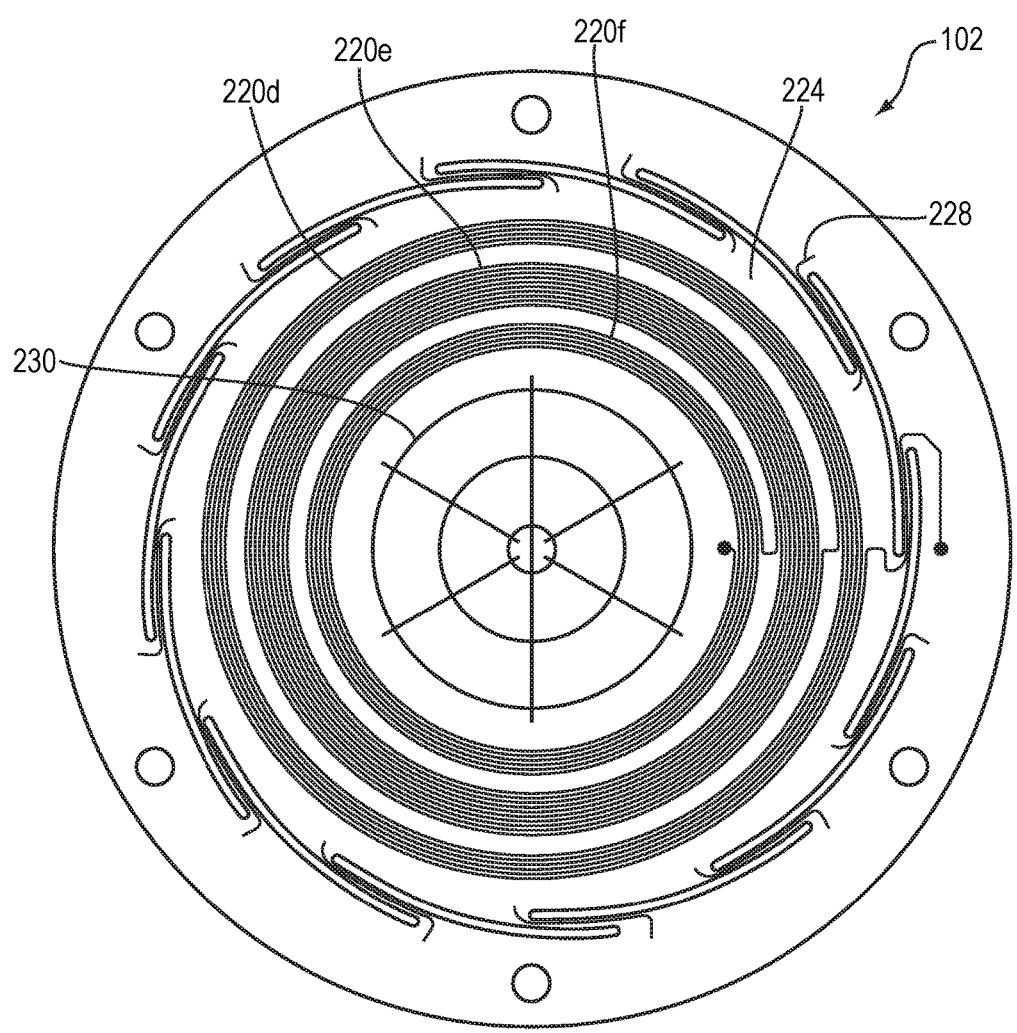
FIG. 2B is a bottom plan view of the interior of the diaphragm illustrated in FIGS. 1A-1C.

With reference to FIG. 2A, the central region 215 of the movable diaphragm portion 204 is domed upward (out of the page) as shown in FIG. 1B, while in FIG. 2B, the central portion 215 extends into the page. The coil 208 is coupled (i.e., attached) to the diaphragm and may cover 50% to 75% of the area of the diaphragm. The coil 208 may take the form of concentric annular regions or "subcoils" representatively indicated at 220*a*, 220*b*, 220*c* in FIG. 2A. In one example, the coil 208 includes a plurality of subcoils 220 disposed both on the top portion 222 of the diaphragm 102 shown in FIG. 2A and corresponding regions of the bottom portion 224 of the diaphragm 102 shown in FIG. 2B. For example, subcoils 220*a*, 220*b*, 220*c* may have counterparts 220*d*, 220*e*, 220*f* as shown in FIG. 2B. A plurality of connector pads 226 are disposed on the top portion 222 of the diaphragm 102 to facilitate electrical connection to the coil 208.

In illustrated embodiment, the subcoils 220*a*-220*f* are connected in series. Each end of the overall coil 208 is connected to one of the connector pads 226. For example, a portion of the conductor of the coil 208 may enter and exit the movable portion 204 of the diaphragm 102 over the body portion 214 of one of the leaf springs 218. Dummy conductors 228 are disposed in the between the remaining slot pairs so as to maintain a substantially similar compliance among the leaf springs.

In one embodiment, the subcoils 220 disposed on the top portion 222 are each substantially physically aligned with corresponding subcoils 220 disposed on the bottom portion 224 of the diaphragm 102, forming subcoil pairs. For example, the subcoil 220*a* may be physically aligned with subcoil 220*f* to form a subcoil pair 220*a*-220*f*. Similarly, the subcoil 220*b* may be physically aligned with subcoil 220*e* to form another subcoil pair 220*b*-200*e*. And finally, the subcoil 220*c* may be physically aligned with subcoil 220*d* to form yet another subcoil pair 220*c*-220*d*. The direction of winding of the conductors of the subcoil pairs is such that a current flowing in each element of a subcoil pair will flow in the same direction. For example, the direction of the current flowing through the subcoil pair 220*a*-200*f* will be the same. Similarly, the direction of the current flowing through the subcoil pair 220*b*-200*e* will be the same, and the direction of the current flowing through the subcoil pair 220*c*-200*d* will be the same. The lengths of the subcoil conductors may be selected to generate a substantially uniform force across the subcoils. For example, the lengths of the conductors in each of the subcoil pairs may be different so as to generate a substantially uniform force across the subcoils.

In one example, a copper-clad flexible (e.g., polyimide) printed circuit board (PCB) may be used to fabricate the coil 208. For example, by selectively etching the copper layer on the PCB, various subcoils may be fabricated thereon. In one example, selectively etched copper-clad flexible PCB may be used for both the diaphragm 102 and the coils 208. In some embodiments, a stiffener 230 may be selectively disposed in an inner portion of the movable portion 204 so as to maintain a substantially constant mechanical impedance for the movable portion 204 of the diaphragm 102. The stiffener 230 and/or the dummy conductors 228 may also be formed by selectively etching the copper layer on the PCB. The slots 206 may be formed, as noted above, by laser cutting.

In another approach, conductive ink is selectively printed (e.g., by deposition or other additive technique) on a substrate to form the coil 208 thereon. In yet another approach, Electroless Nickel Immersion Gold (ENIG) may be selectively deposited on a substrate to form the profile of the coil 208 on the substrate, which acts as a seed layer. Over the ENIG seed layer, the coil may be electroplated in aqueous electrolyte with copper to get a coil of required thickness. Once again, the substrate serves as the diaphragm 102. Alternative methods known in the art may be used including but not limited to microelectromechanical systems (MEMS) techniques, such as conventional deposition and etching processes, and the formed coil may be mechanically wound according to the scale of the sensor being fabricated.

It should be noted that in some implementations, a moving magnet is used instead of a moving coil. This can be accomplished by locating the magnet on the movable portion 204 of the diaphragm 102 and placing the coils on the fixed portion 202 of the diaphragm or on a parallel adjacent layer.

Figure 2C:
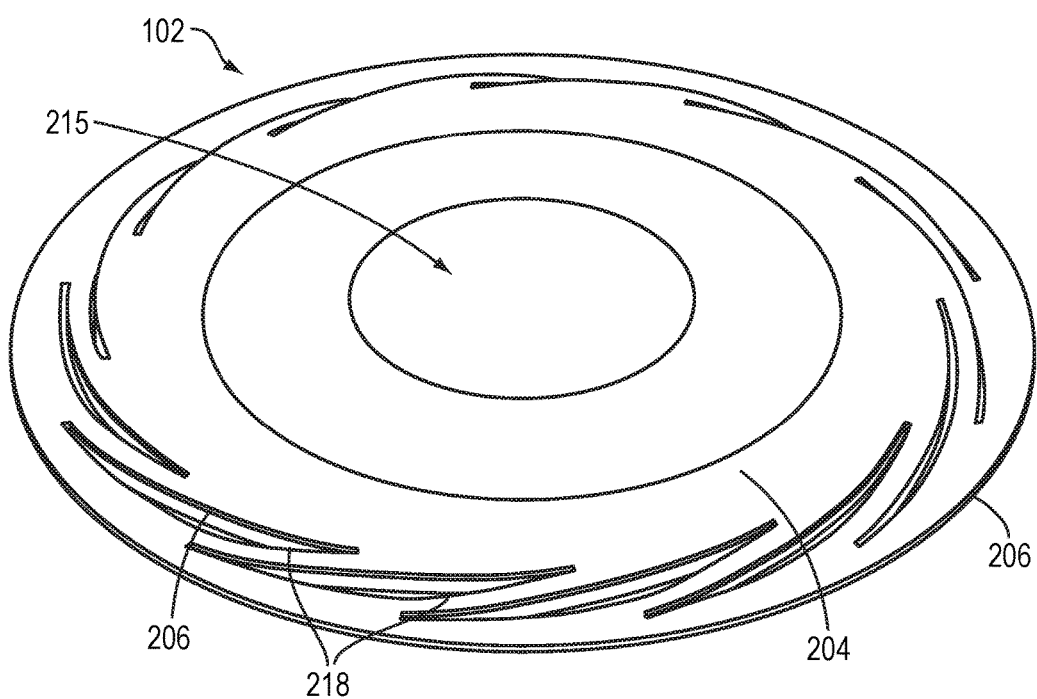
FIG. 2C is a perspective view illustrating operation of the leaf springs of the diaphragm illustrated in FIGS. 1A-1C.

The operation of the leaf springs is best seen in FIG. 2C. As the movable portion 204 rises with respect to the fixed portion 206 (under the action of the coil 208, not shown in FIG. 2C), the leaf springs 218 permit but restrain this movement with a degree of compliance established as described above. The movable portion 204 may be biased with respect to the fixed portion 206 so that, in its normal (rest) state, it resides above or below the plane of the fixed portion. The movable portion 204 reaches coplanarity with the fixed portion 206 only when pressure is applied to the diaphragm 102 by, e.g., target tissue contact with the connected pickup 104. The operational state of the diaphragm 102 may be the coplanar state or may be a biased state according to the referential direction and degree of target tissue contact. The optimal bias is usually within the range of 0.1-3 mm of the normal state for a sensor with a diaphragm diameter between 5 mm and 50 mm. In certain embodiments, the diaphragm 102 and/or attached pickup has adjacent structures to limit the magnitude of deflection (e.g., to a displacement range within ±5 mm of the normal state, ±3 mm of the normal state, or other displacement) to prevent irreversible damage to the diaphragm 102. An adjacent structure may reduce or completely prevent the diaphragm from producing a signal, for example, thereby indicating that additional or less pressure is required at the contact between the structure and the pickup 104. The sensor 100 may include a pressure sensor (e.g., disposed adjacent to the pickup 104) to measure the pressure applied to the pickup 104. Suitable pressure sensors include piezoelectric, piezoresistive, capacitive, and optical sensors.

Figure 3A:
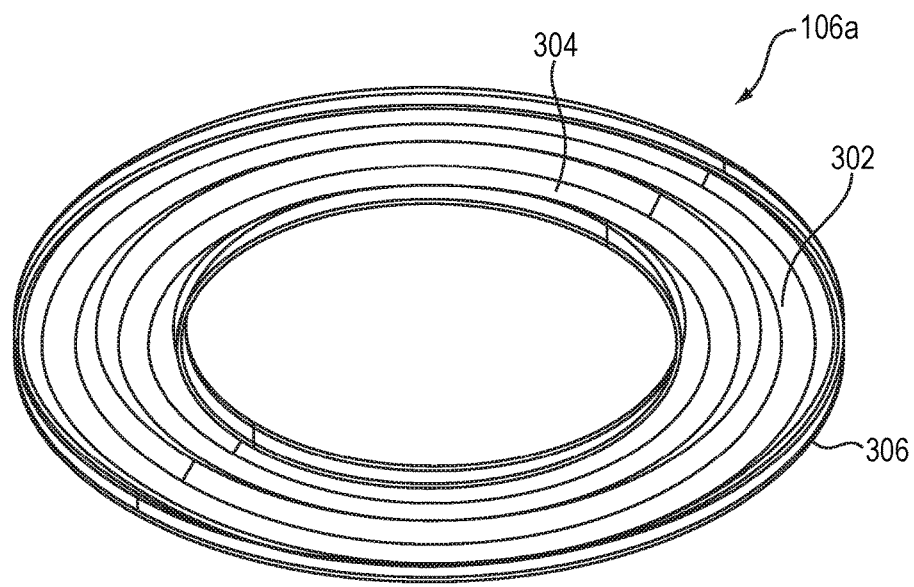
FIGS. 3A and 3B show bottom and top views, respectively, of the top magnet assembly in accordance with one embodiment of the invention.
Figure 3B:
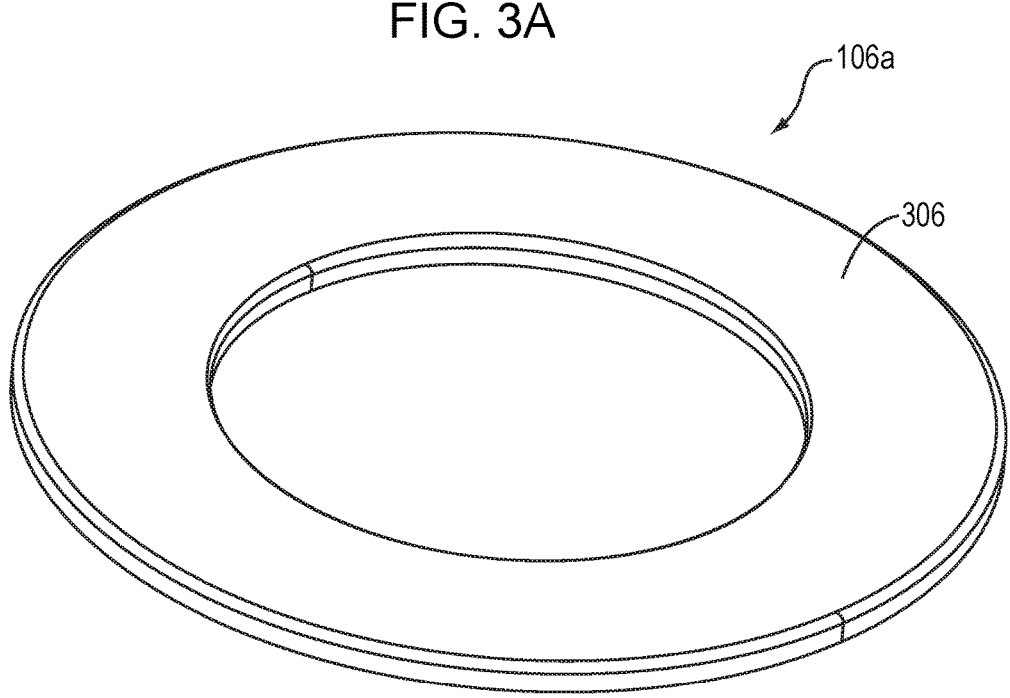
Figure 3C:
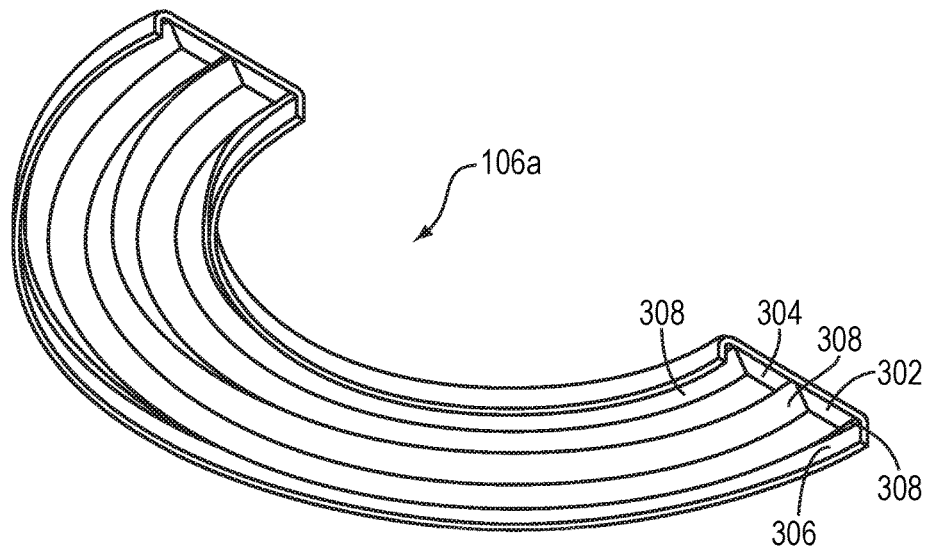
FIG. 3C shows a portion of the top magnet assembly in greater detail.
Figure 3D:
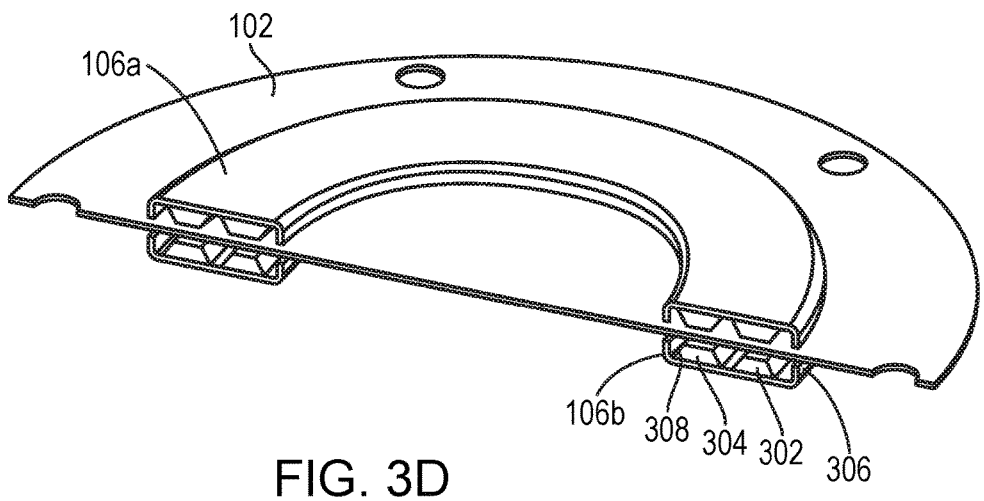
FIG. 3D is a sectional perspective view of the top and bottom magnet assemblies in accordance with one embodiment of the invention.

FIGS. 3A-3D illustrate various features of the top magnet assembly 106*a* and bottom magnet assembly 106*b*. The top magnet assembly 106*a* includes an outer ring magnet 302 and an inner ring magnet 304 spaced apart and retained within a holder 306. The outer ring magnet 302 and inner ring magnet 304 may be compression bonded neodymium ring magnets of substantially same width, with isosceles trapezoid cross-sections at about 45°±5°. The holder 306 may be made of a soft magnetic material with high inductance (e.g., AISI 1018 mild/low carbon steel), for example. As shown in FIG. 3C, the side surface 308 of the outer ring magnet 302 and inner ring magnet 304 represent the inclined surfaces of the trapezoidal cross-section. The bottom magnet 106*b* has a similar construction. FIG. 3D shows the top and bottom magnet assemblies 106*a*, 106*b* operatively disposed in contact with the diaphragm 102.

Figure 1C:
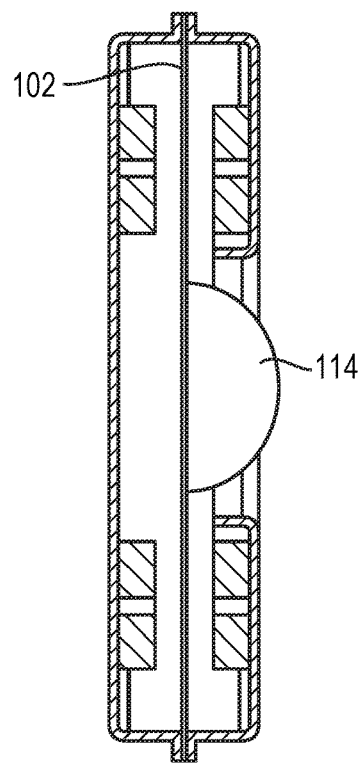
Figure 4A:
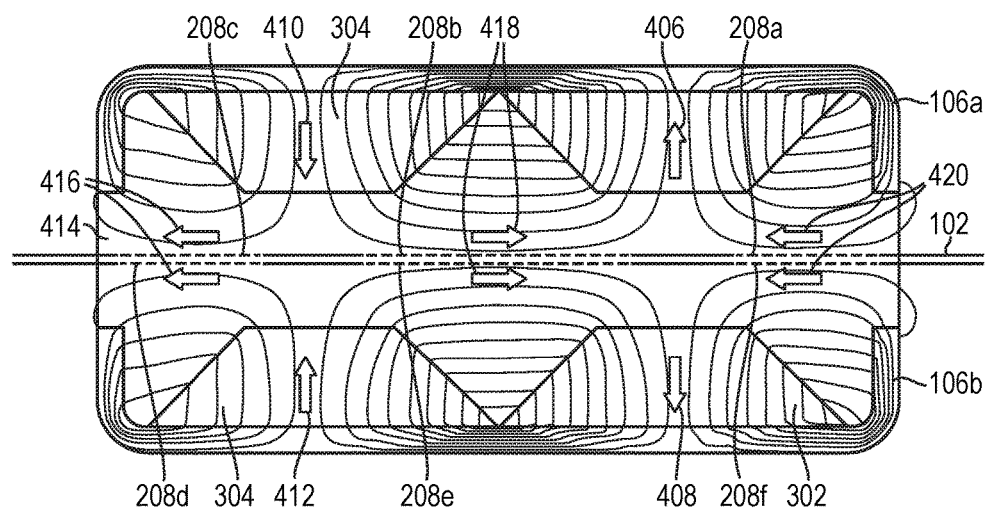
FIG. 4A is another sectional elevation of the sensor of FIG. 1A showing magnetic field lines generated by the top magnet assembly and the bottom magnet assembly.

FIG. 4A shows yet another sectional view of the sensor 100 as previously described with reference to FIGS. 1A-1C. The top magnet assembly 106*a* is retained within the top case 108 (not shown in FIG. 4A). For example, the top magnet assembly 104 may be glued with the top case with an epoxy, and similarly, the bottom magnet assembly 106 may be glued with the bottom case 112 (also not shown in FIG. 4A) with an epoxy. The diaphragm 102 is disposed between the top and bottom magnet assemblies 106*a*, 106*b* so as to operatively dispose the subcoils relative to the top magnet assembly 104 and the bottom magnet assembly 106. FIG. 4A additionally shows the electro-magnetic interaction between the top magnet assembly 106*a*, the bottom magnet assembly 106b and the subcoil pairs of the coil 208 disposed on the diaphragm 102. In this example, the outer ring magnets 302 of the top and bottom magnet assemblies 106a, 106b are magnetized so as to oppose each other, as indicated by arrows 406, 408. The inner ring magnets 304 of the top and bottom magnet assemblies 106a, 106b are magnetized so as to attract each other, as indicated by arrows 410, 412. The spacing between the top and bottom magnet assemblies 106a, 106b defines an air gap 414. The subcoil pairs of the coil 208 are disposed in the air gap 414 and subjected to the magnetic field generated by the outer ring magnets 302 and inner ring magnets 304 of the magnet assemblies 106a, 106b. In other words, the magnet assemblies create a magnetic field substantially in the plane of the diaphragm 102 and perpendicular to the flow of current through the subcoil pairs of the coil 208. More specifically, the subcoil pairs 208c-208d are subjected to magnetic field in the direction indicated by arrow 416; the subcoil pairs 208b-208e are subjected to magnetic field in the direction shown by arrow 418; and the subcoil pairs 208a-208f are subjected to magnetic field in a direction shown by arrow 420. The average radius of the planar magnet sub-assembly is selected to correspond with the average nodal radius of the fundamental mode of flexural vibration of the diaphragm 102. A sparsely modal system (as described below) is optimally driven at the nodes rather than anti-nodes because less displacement is needed at that first resonant frequency.

Figure 4B:
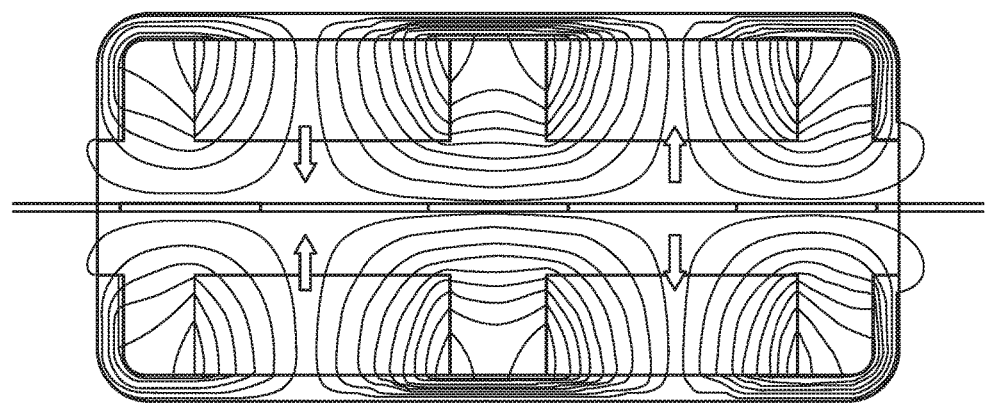
FIG. 4B is another sectional elevation of the sensor of FIG. 1A with rectangular rather than trapezoidal magnets.

FIG. 4B shows the magnetic field within the magnet assembly with four magnets having rectangular rather than trapezoidal cross-section but using the same amount of material as in FIG. 4A. Various other embodiments may use different magnet shapes or placements as long as the interaction with the subcoil pairs are maintained. In certain embodiments, the subcoil pairs exist as three pairs, four pairs, five pairs, etc.

Figure 4C:
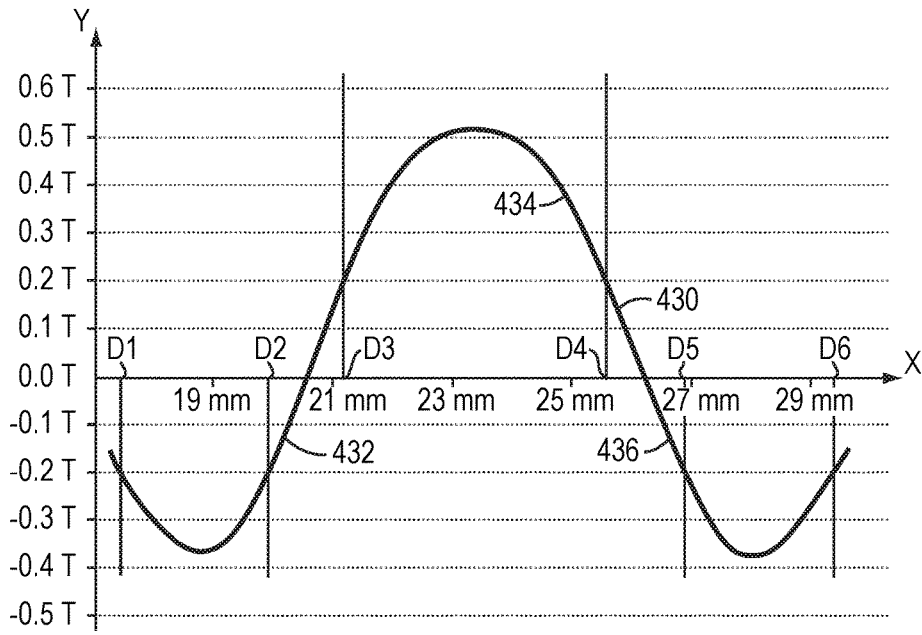
FIG. 4C depicts magnetic field strength generated by top and bottom magnet assemblies from the center of a diaphragm in accordance with one embodiment of the invention.

In FIG. 4C, the plot 430 shows the magnetic field strength generated by the top and bottom magnet assemblies from a center of the diaphragm. In particular, the x-axis shows the distance from the center of the diaphragm and y-axis shows the magnetic field strength at various locations of the diaphragm, along the radius thereof. The portion 432 of the plot 430 (below the x-axis) shows the magnetic field strength imparted in the vicinity of the subcoil pairs 208c-208d, the portion 434 (above the x-axis) shows the magnetic field strength imparted in the vicinity of subcoils 208b-208e, and the portion 436 (below the x-axis) shows the magnetic field strength imparted in the vicinity of the subcoils 208a-208f. The subcoils may be selectively placed on the diaphragm so that the magnetic field strength imparted on the subcoil is above a threshold value. For example, if the threshold value for the magnetic field strength is chosen to exceed ±0.2 Tesla, the subcoils 208c-208d are placed between a distance of D1 and D2 from the center of the diaphragm, the subcoils 208b-208e are placed between a distance of D3 and D4 from the center of the diaphragm, and the subcoils 208a-208f are placed between a distance of D5 and D6 from the center of the diaphragm.

As one skilled in the art will appreciate, when a current flows through the subcoil pairs of the coil 208, the amount of force generated depends on the length of the subcoil and the magnetic field strength to which the subcoil is subjected. In the illustrated embodiment, the subcoil pairs 208b-208e are subjected to a higher magnetic field strength than the subcoil pairs 208c-208d and 208a-208f. It is of course possible to select the subcoil winding length to generate a substantially uniform force across all the subcoils, which is typically beneficial. By distributing the force uniformly across the subcoils, and therefore across the diaphragm, there is less echoing (or distortion) as sound travels in a single plane. Distortion reduction, especially at low frequencies, improves the signal-to-noise ratio of the signal captured by the sensor. Moreover, a uniform force will beneficially minimize bending moments in the diaphragm 102, which is particularly advantageous in the case of multilayer structures as described below.

In one embodiment, the direction of current flowing through the subcoil pairs is chosen such that the movable portion of the diaphragm 102 moves in a single direction. In this example, the subcoil pair 208b-208e is subjected to a magnetic field in the direction indicated by arrow 418, but the subcoil pairs 208a-208f and 208c-208d are subjected to a magnetic field in the direction as shown by arrows 416, 420, which are opposite to the direction shown by arrow 418. In order to move the movable portion of the diaphragm 102 in the same direction, the direction of flow of current in subcoil pair 208b-208e will be opposite to the direction of flow of current in subcoil pairs 208a-208f and 208c-208d.

Figure 4D:
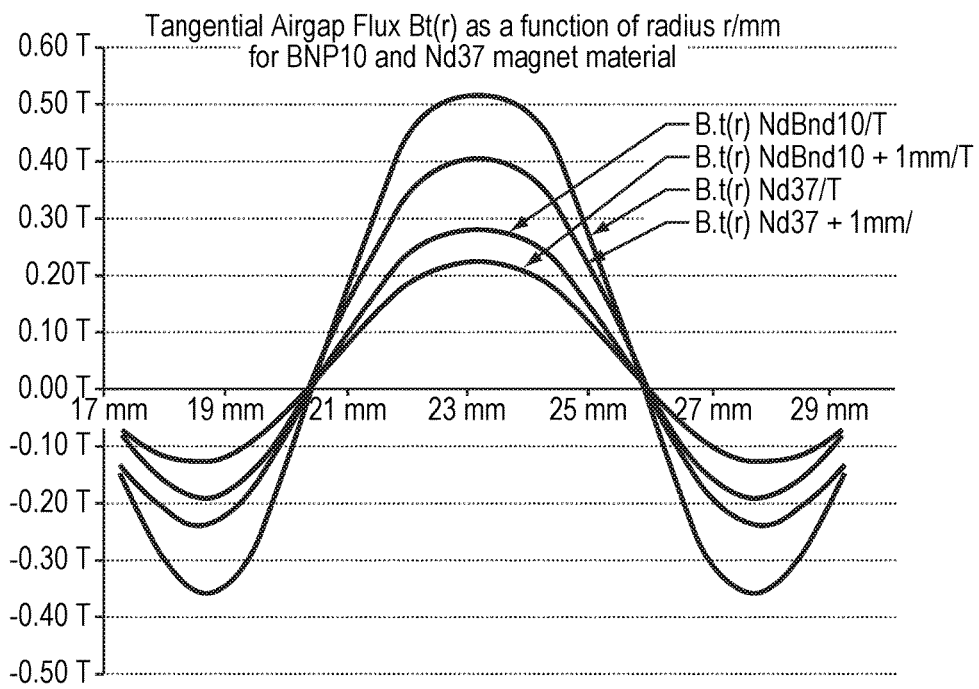
FIG. 4D depicts a simulation showing the tangential air-gap flux density as a function of radius in accordance with one embodiment of the invention.
Figure 4E:
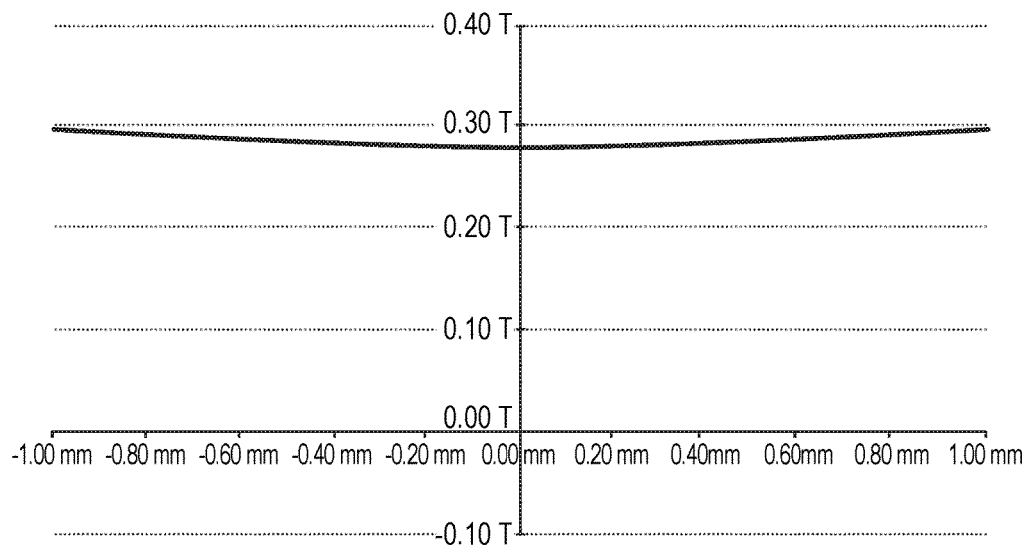
FIG. 4E depicts the magnetic flux density as a function of height from the diaphragm center.

FIG. 4D depicts a finite element analysis (FEA) simulation of the magnet structure showing the axisymmetric tangential air-gap flux density B·t(r) as a function of radius r (mm) for 1 mm and 2 mm magnet pole separation for the BNP10 and Nd37 magnet material. FIG. 4E depicts the magnetic flux density B·n(z)/Tesla as a function of height z (mm) from diaphragm center at magnet structure center r=23.0 mm for BNP10 magnet material.

Figure 5A:
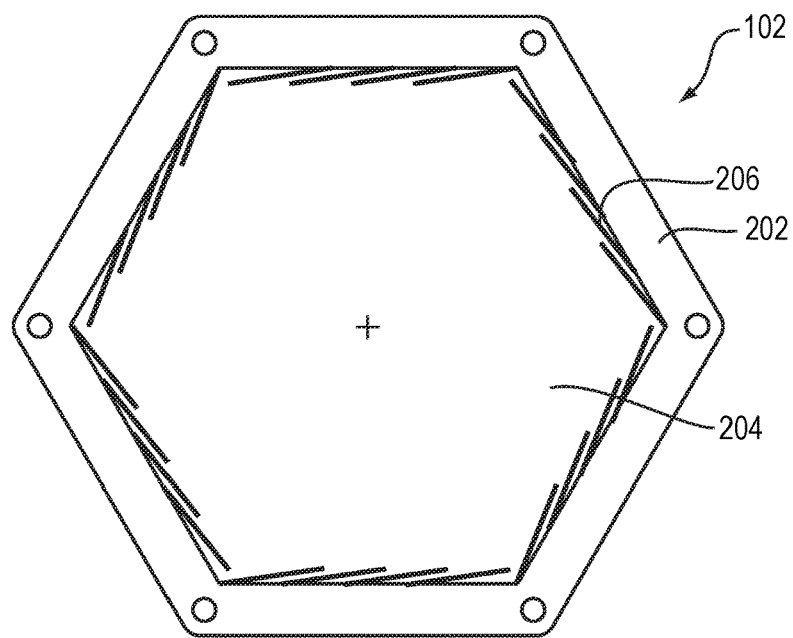
FIGS. 5A-5F are top plan view of alternative diaphragm shapes.
Figure 5B:
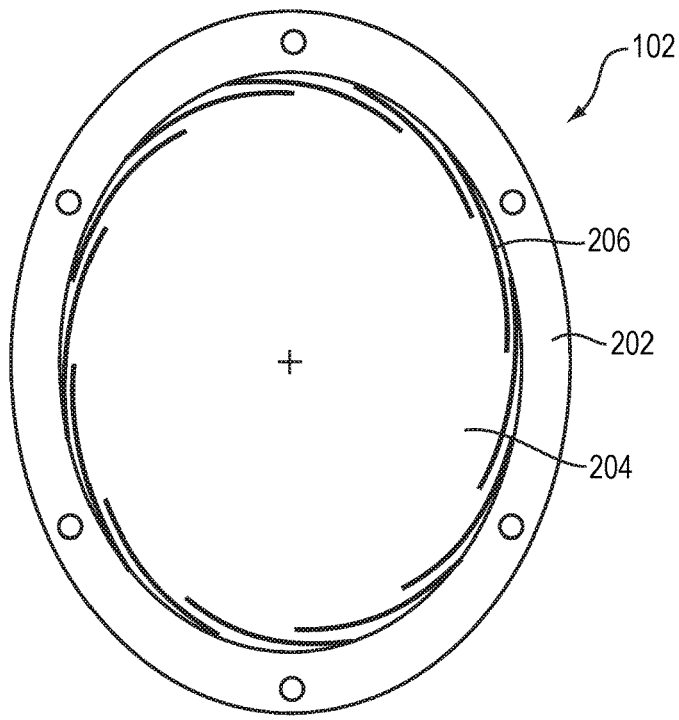
Figure 5C:
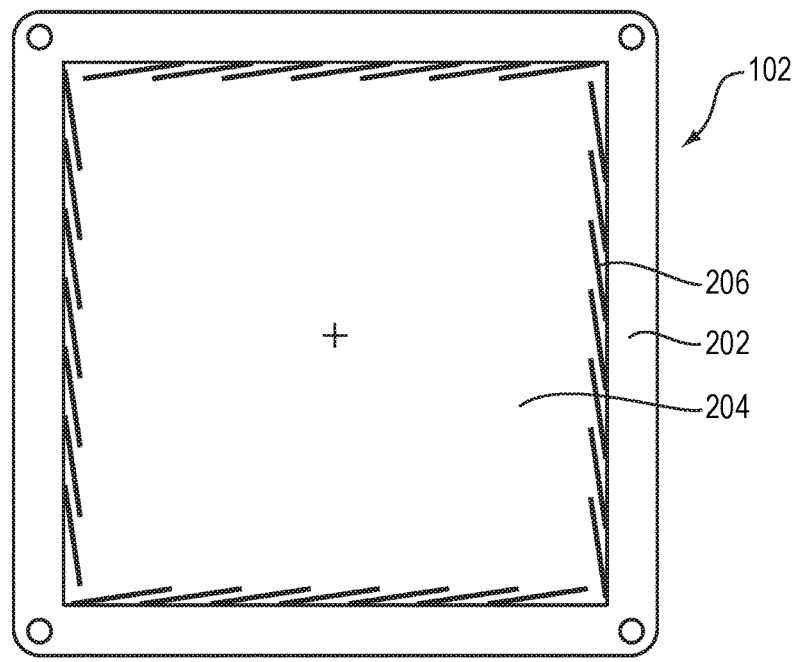
Figure 5D:
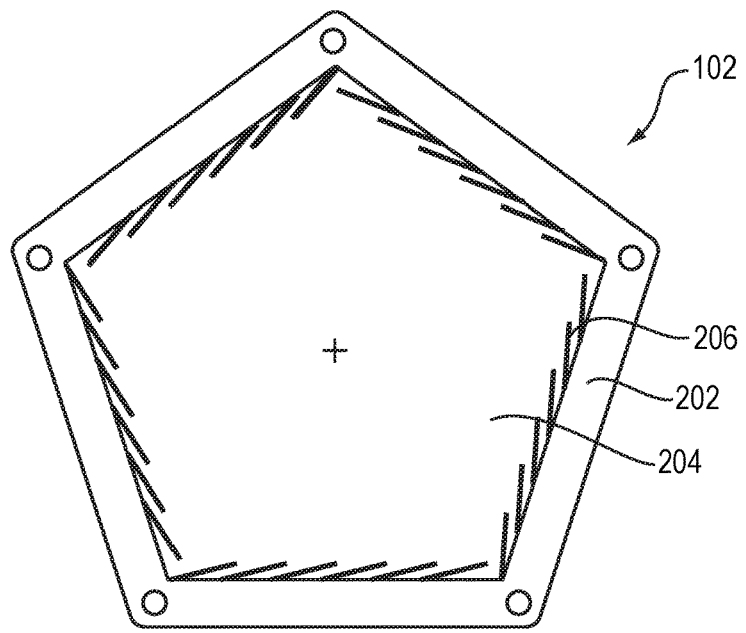
Figure 5E:
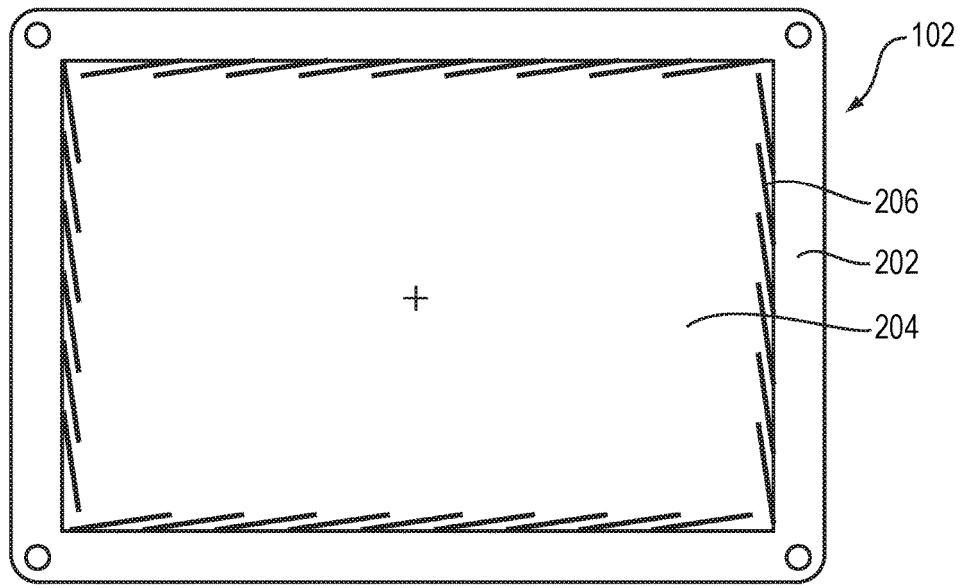
Figure 5F:
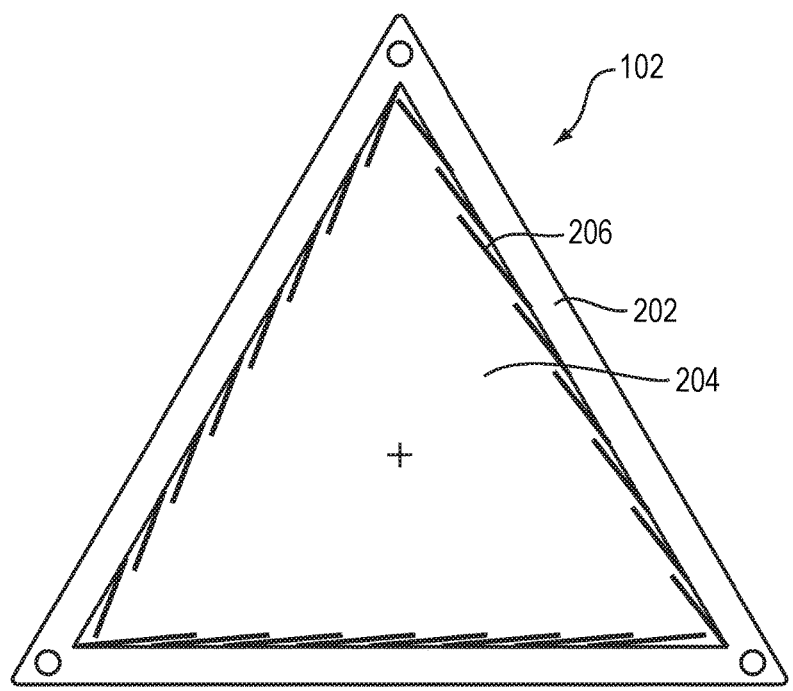

In the foregoing example, the shape of the sensor 100 was substantially circular. However, other shapes, such as those with a high axial symmetry, may be used. For example, FIG. 5A shows a diaphragm 102 in a hexagonal shape, with a plurality of leaf springs 206 separating the fixed portion 202 and the movable portion 204. FIG. 5B shows a diaphragm 102 in an oval shape, with a plurality of leaf springs 206 separating the fixed portion 202 and the movable portion 204. FIG. 5C shows a diaphragm 102 in a square shape, with a plurality of leaf springs 206 separating the fixed portion 202 and the movable portion 204. FIG. 5D shows an example diaphragm 102 in a pentagonal shape, with a plurality of leaf springs 206 separating the fixed portion 202 and the movable portion 204. FIG. 5E shows a diaphragm 102 in a rectangular shape, with a plurality of leaf springs 206 separating the fixed portion 202 and the movable portion 204. FIG. 5F shows a diaphragm 102 in a triangular shape, with a plurality of leaf springs 206 separating the fixed portion 202 and the movable portion 204.

The diaphragm 102 may take various forms in accordance with the present invention. It is desirably isotropic, and in some embodiments the coils are integrated within a composite sandwich panel system to form the diaphragm 102. This permits the diaphragm to be substantially mechanically isotropic (i.e., the mechanical impedance of the diaphragm remains constant over some minimum scale) over its entire area of the diaphragm, permitting sparsely modal behavior—i.e., the first vibrational mode occurs close to and/or above the frequency band of interest, in typical applications about 1 Hz to 10 kHz. To enhance contact with the skin, in particular skin covered with hair or, in the case of animal subjects, fur, the diaphragm 102 (in particular, the pickup 104) may, in some embodiments, be provided with surface features such as pimples, shallow dimples, or corrugations.

Diaphragm transducer configurations suitable for use herewith also include more traditional piston microphone arrangements with conventional capacitive (rather than coil-based) diaphragms. With a pickup attached, these are very efficient at coupling the longitudinal pressure waves generated inside the body when they reach the skin surface while rejecting the transverse and flexural waves on the surface of the skin. The pick-up desirably maximizes the signal-to-noise ratio by mechanically rejecting unwanted noises. For example, longitudinal sounds emanating directly from organs inside the body such as heart murmurs, intestinal movements or shoulder tendon clicks are the first vibrations to reach the pickup, while the system mechanically rejects irrelevant acoustic signals such as reflections, skin movement or sound from surrounding tissues. As described below, a domed, stiff pickup can further enhance the first vibrational mode measurements from piston transducers coming from the target organ.

The diaphragm may be formed from, for example, a composite sandwich panel structure comprising or consisting of top and bottom layers (or "skins") of copper-clad polyimide sandwiching a core, e.g., a rigid, closed-cell polymeric foam such as ROHACELL 31IG polymethacrylimide (PMI). The core and/or one or both of the skins may be a monolithic panel (e.g., isotropic in the case of an acrylic panel of, for example, 1.5 mm thickness as compared to a sandwich composite panel of greater thickness or two or more sections fused together), which function acoustically as having zero thickness. The copper cladding may be etched to ensure isotropic mechanical impedance of 10% or less of the shortest planar dimension (e.g. diameter) of the diaphragm.

The sandwich panel skins can readily be made with standard flex printed circuit (FPC) fabrication techniques using commercially available high-performance copper-clad polyimide such as Panasonic FELIOS R-F775 (8.7 µm to 17.4 µm Cu foil on 12.7 µm to 25.4 µm polyimide substrate) material, or can alternatively be made using standard RFID antenna fabrication techniques using aluminum (5 µm to 10 µm) clad PET/polyester films (5 µm to 25 µm). Standard FPC copper-clad laminates PEEK (e.g., a XT/duroid 8000 and XT/duroid 8100 from Rogers Corporation) and LCP (e.g., ULTRALAM 3000 (3850/3850HT)) from Rogers Corporation) can be used to fabricate panels with local stiffening by thermoforming a single central dome or multiple domes or corrugations to stiffen the central region and/or create contact points for the sensor. The dome 104 may be fabricated not for further stiffening to raise the first mode but instead to provide a contact point with the biological tissue (e.g. probe), thereby cancelling non-first mode vibrations (relative motion, bending waves, etc.) resulting in the diaphragm's modal contributions having a zero mean volume velocity, thereby isolating only the diaphragm's pistonic response. At the same time, a contact point for focusing the pickup may be created by a very high stiffness glued-on dome made from e.g., one or more stiff carbon or boron fiber composite panels. At the size (e.g., 10 mm to 30 mm) suitable for transducer sensors for bodily sounds, the bending stiffness increases and the panel of the transducer remains pistonic or very sparsely model in the frequency band of interest. The dome 104 plays a critical role in rejecting non-pistonic motion, and thereby allowing the system to pick up sounds from the body without interference from echoes.

In an alternative embodiment, the diaphragm may be an isotropic graphene skin composite sandwich panel, which may be fabricated using laser cutting or stamping from a mechanical press. Such constructions provide increased stiffness for the skins and reduced areal density for the mechanical properties of the panel, as well as increased conductivity for the laser-cut planar voice-coils.

Numerous variations are also possible for the diaphragm 102 and, in particular, the pickup 114, which may be further optimized to accommodate a variety of viscoelastic impedances found in the target living tissue. Most simply, the pickup 114 will behave like an impedance transformer as it couples the tissue's longitudinal pressure waves reaching the skin surface to the diaphragm, which supports transverse bending waves. The pickup 114 is therefore optimally very stiff and light. An ultrathin carbon fiber dome is ideal for many applications, although other optimizations may be made for specific target tissues.

In certain embodiments, the pickup 114 (e.g., dome) is manufactured to size, shape, stiffness and thickness parameters to optimize interfacing to the target tissue. For example, the target tissue region may be divided into primarily muscle, adipose, or bone (e.g., the pectoral muscles of the superior ventral torso, the stomach region below the rib cage, scapula, respectively). A stiff, thin pickup dome will advantageously interface to the adipose tissue compared to a larger pickup dome, which would more advantageously interface to bone tissue. The function of the dome is to transfer longitudinal pressure waves in the body reaching the tissue surface to transverse flexural waves of the panel, albeit before the onset of the first vibrational mode of the diaphragm. This fundamental mode frequency, as it is called, depends in general on the square root of material's elastic stiffness (Young's modulus, E/GPa) divided by its mass density ($\rho$, kg/m$^3$). This dependency is simulated in FIG. 4F, which includes finite element analysis simulations to compare flat disks and domes of the same dimension and also the effect of materials. In particular, the dependency is depicted graphically in FIG. 4G, which compares carbon fiber-reinforced plastic (CFRP) pickups with other materials such as stainless steel, glass fiber reinforced plastic, polymethylmethacrylate (Acrylic, Plexiglas, Perspex, Lucite) PMMA, and polycarbonates, illustrating the performance benefits of stiffer, lighter material such as CFRP, which has a very high yield strength. It should be noted that although the lowest mass of the pickup is desirable there is in effect a lower limit to panel thickness set by collapse of the dome due to yielding or buckling.

Accordingly, the precise characteristics of the pickup 114 may be optimized for, e.g., haptic reproduction of a particular target tissue. In addition, it should be noted that the coils 220 may be planar as described above or can have a more conventional helical design and be attached perpendicular to the diaphragm. In another embodiment, tripod-like assemblies may be used for attaching transducers to uneven surfaces while maintaining a "displacement stop" that prevents too much pressure being applied to the pick-up surface.

Alternatively or in addition, various gels that are advantageously impedance-matched to the mechanical impedance of various tissues may be applied to either the pickup or target tissue prior to application of the sensor. (Thus, whereas the pickup dome 114 has a mechanical impedance mismatched to that of the skin, gels and/or covers placed between the skin and the pickup dome 114 are advantageously impedance-matched to the biotissue (or are extremely thin) to allow the pressure waves through with minimal absorption.) The very thin layer of gel with a similar or matching impedance enhances contact and allows the pressure waves from the tissue to travel to the pickup 114 with minimal absorption and potential loss due to disparities between the tissue surface and pickup surface curvatures. The sensor can be optimized to obtain the best impedance by including or applying different gels, soft gel-attachments, or material similar to skin, such as silicone rubber, pure silicones, liquid suspensions, gelatinous substances, elastomers, epoxy resins, metals, textiles, as well as nano- and micro-fillers can be incorporated in the skin models to tune their physical properties to maintain a good contact, thereby maximizing the collection of pure tone data with minimal distortion. Any of various conventional techniques of manufacture may be employed to produce the vibro-acoustic sensor as described herein. Scaling to miniaturization is advantageous in that the mass of the pickup 114 and diaphragm 102 scale by the third power while most of the other electrical and mechanical sensor components scale linearly. This allows most components to be reduced in size with particular benefit for the pickup 114 and diaphragm 102, which can be made disproportionately lighter and stiffer, can take different shapes, and can be made from cost-effective materials rather than ultra-lightweight materials that may be required at larger scales. Although there are limitations to miniaturization, such as the effect of coil size reduction on signal-to-noise ratio, these are straightforwardly balanced against benefits obtained.

In yet another embodiment, the pickup 114 is miniaturized to provide maximal deflection of the diaphragm with minimal force applied. The pickup can be shaped as a narrow dome, a torus, a series of rings, or a corrugated structure; for example the dome may be omitted and a flat or nearly flat surface utilized in conjunction with a gel or other fluid impedance-matched to the skin. Dimples, pimples, corrugations or other features may be provided on the surface of the miniaturized pickup. Further, the pickup may be offset by a specific angle (1° to 45°) or by manufacturing the diaphragm with a specific offset by altering the cantilevered suspension or by placement of shims. Improving the sensitivity of the sensor to forces non-perpendicular to the diaphragm is beneficial for embodiments requiring sensors to be placed in a non-planar array. In another embodiment, the sensor-pickup systems can be connected to a system of sensors various orientations in order to surround a body part, such as the knee or shoulder which are closed compartments consisting of various systems of materials including tendons, viscoelastic interface, bone and fluid.

Figure 6A:
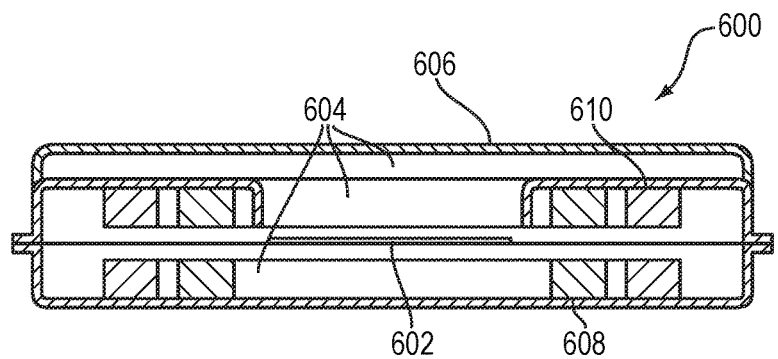
FIGS. 6A and 6B are, respectively, a sectional elevation and an exploded view of a sensor embodiment including a ferrofluid.
Figure 6B:
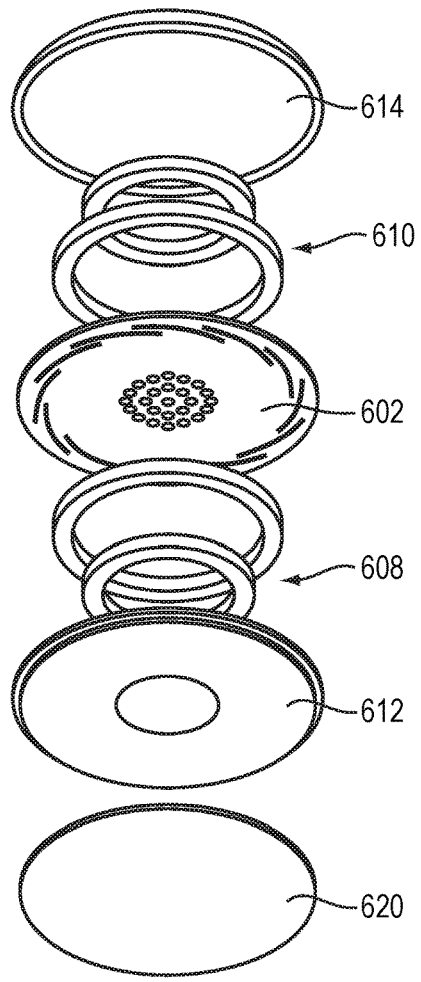
Figure 6C:
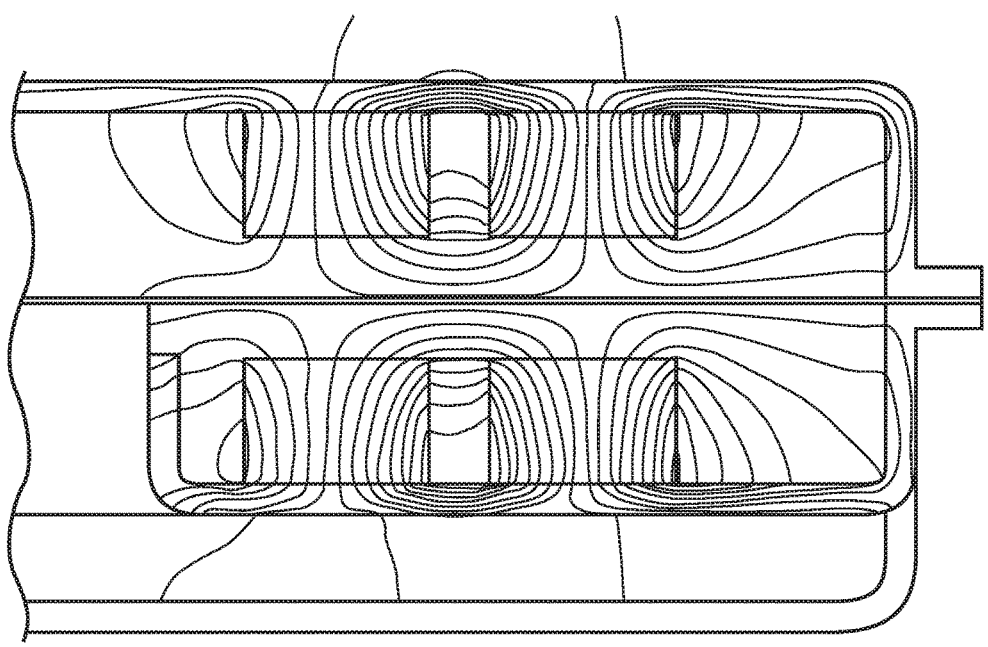
FIG. 6C is another sectional elevation of the sensor of FIGS. 6A and 6B showing magnetic field lines generated by the magnets.

In another alternative, the stiff pickup 114 is replaced by one or more magnetic fluids (e.g., a ferrofluid, a superparamagnetic fluid, ferroputties etc.) combined with a magnet to remove the airgap. One embodiment is shown in FIGS. 6A-6C in which a vibro-acoustic sensor 600 with a centrally perforated diaphragm 602 (e.g., 4.0 mm in diameter) is suspended in a ferrofluid 604 contained within a sealed environment. As is well-known, ferrofluids are colloidal liquids that include nanoscale ferromagnetic or ferrimagnetic particles suspended in a carrier fluid (usually an organic solvent or water), and become strongly magnetized in the presence of a magnetic field. The diaphragm 602 may have a slotted multileaf cantilever suspension as described above, and the illustrated embodiment includes four circular magnets having square cross-sections and organized into two sets 608, 610 each having two concentric magnets. The ferrofluid 604 and magnets 608, 610 are sealed within mating housing members 612, 614; the housing member 614 may be shaped for acoustic pickup, and may be covered by a gel surface member 620 that is impedance-matched to biological tissue. FIG. 6C shows the magnetic field within the assembly 600.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A sensor device comprising:
    a diaphragm having an outer peripheral portion and an inner portion, the inner portion being attached to the outer portion by a plurality of discrete, angularly spaced-apart leaf springs constraining relative movement between the inner portion and the peripheral portion;
    a coil disposed over at least one side of the diaphragm; and
    at least one magnet operatively disposed with respect to the coil to cause current to flow through the coil upon relative movement between the inner portion and the peripheral portion.

2. The sensor device of claim 1, wherein the inner portion is fixed and the outer peripheral portion is movable with respect thereto.

3. The sensor device of claim 1, wherein the outer portion is fixed and the inner portion is movable with respect thereto.

4. The sensor device of claim 3, wherein the outer fixed portion of the diaphragm has a shape and the inner portion is defined within a plurality of slots through the diaphragm and arranged in a series, wherein (i) the series defines a closed sequence concentric with and having the shape of the outer fixed portion, and (ii) the series of slots are arranged such that each pair of slots within the series is parallel and has an overlap portion and a non-overlap portion, the overlap portion defining an intervening strip corresponding to one of the leaf springs.

5. The sensor device of claim 4, wherein the slots are filled with a thixotropic material.

6. The sensor device of claim 1, wherein the coil and the at least one magnet are circular.

7. The sensor device of claim 1, wherein the at least one magnet is a pair of magnet assemblies disposed on opposite sides of the diaphragm, each of the assemblies including at least two concentric magnets.

8. The sensor device of claim 7, wherein each of the magnets has an isosceles trapezoid cross-section with an angle of 45°±5°.

9. The sensor device of claim 1, wherein the coil occupies 50% to 75% of a surface area of the diaphragm.

10. The sensor device of claim 1, further comprising a pickup structure extending from the diaphragm for contact with a biological tissue surface.

11. The sensor device of claim 10, wherein the diaphragm has modal contributions with zero mean volume velocity to isolate a pistonic response of the diaphragm for voltage generated in a direction perpendicular to the diaphragm.

12. The sensor device of claim 10, wherein the pickup structure is a dome.

13. The sensor device of claim 12, wherein the dome has surface features.

14. The sensor device of claim 13, wherein the surface is pimpled, dimpled or corrugated.

15. The sensor device of claim 12, wherein the pickup structure has a mechanical impedance mismatched with respect to a target surface.

16. The sensor device of claim 1, wherein the diaphragm is a composite sandwich panel including a core and a monolithic panel on each side of the core.

17. The sensor device of claim 16, wherein the panels are copper foil-clad flexible printed circuit polymer film.

18. The sensor device of claim 17, wherein the copper is etched to ensure isotropic mechanical impedance of 10% or less of a shortest planar dimension of the diaphragm.

19. The sensor device of claim 16, wherein the panels are fabricated from a graphene composite structure.

20. The sensor device of claim 19, wherein the graphene is etched to ensure isotropic mechanical impedance of 10% or less of a shortest planar dimension of the diaphragm.

21. The sensor device of claim 1, wherein the diaphragm is asymmetrically biased in an unenergized state.

22. The sensor device of claim 21, wherein the bias is in the range of 0.1 mm to 3 mm.

* * * * *